United States Patent
Carrell et al.

(10) Patent No.: US 10,977,812 B2
(45) Date of Patent: Apr. 13, 2021

(54) DEFORMATION CORRECTION

(71) Applicant: Cydar Limited, Barrington (GB)

(72) Inventors: Tom Carrell, Barrington (GB); Graeme Penney, Barrington (GB); Andreas Varnavas, Barrington (GB)

(73) Assignee: Cydar Limited, Barrington (GB)

( * ) Notice: Subject to any disclaimer, the term of this patent is extended or adjusted under 35 U.S.C. 154(b) by 69 days.

(21) Appl. No.: 16/368,220

(22) Filed: Mar. 28, 2019

(65) Prior Publication Data

US 2019/0304108 A1 Oct. 3, 2019

(30) Foreign Application Priority Data

Mar. 29, 2018 (GB) ..................... 1805299

(51) Int. Cl.
*G06T 7/33* (2017.01)
*G06T 7/73* (2017.01)
(Continued)

(52) U.S. Cl.
CPC .............. *G06T 7/337* (2017.01); *A61B 34/20* (2016.02); *G06T 7/74* (2017.01); *A61B 2017/00694* (2013.01); *A61B 2017/564* (2013.01); *A61B 2034/2065* (2016.02); *A61B 2090/365* (2016.02); *A61B 2090/3762* (2016.02);
(Continued)

(58) Field of Classification Search
CPC . G06T 2207/10121; G06T 2207/10081; G06T 2207/30101; G06T 2207/30012; G06T 7/30; G06T 7/337; G06T 2207/10064; G06T 2207/30004;
(Continued)

(56) References Cited

U.S. PATENT DOCUMENTS 9,262,830 B2 * 2/2016 Bakker .................... G06T 7/33
2010/0266220 A1 * 10/2010 Zagorchev ........... A61B 6/5205
382/285
(Continued)

FOREIGN PATENT DOCUMENTS

DE  10 2008 018 387 A1  10/2009
DE  10 2009 039 986 A1  3/2011

OTHER PUBLICATIONS

Huesman et al, "Deformable Registration of Multimodal Data Including Rigid Structures," Jun. 2003, IEEE Transactions on Nuclear Science, vol. 40, No. 3, pp. 389-392 (Year: 2003).*
(Continued)

*Primary Examiner* — Margaret G Mastrodonato
(74) *Attorney, Agent, or Firm* — Sterne, Kessler, Goldstein & Fox P.L.L.C.

(57) ABSTRACT

A method is described for adapting 3D image datasets so that they can be registered and combined with 2D images of the same subject, wherein deformation or movement of parts of the subject has occurred between obtaining the 3D image and the 2D image. 2D-3D registrations of the images with respect to multiple features visible in both images are used to provide point correspondences between the images in order to provide an interpolation function that can be used to determine the position of a feature visible in the first image but not the second image and thus mark the location of the feature on the second image. Also described is apparatus for carrying out this method.

19 Claims, 3 Drawing Sheets

(51) Int. Cl.
  *A61B 34/20* (2016.01)
  *A61B 17/00* (2006.01)
  *A61B 90/00* (2016.01)
  *A61B 17/56* (2006.01)
(52) U.S. Cl.
  CPC .............. *G06T 2207/10064* (2013.01); *G06T 2207/10081* (2013.01); *G06T 2207/30012* (2013.01); *G06T 2207/30101* (2013.01)
(58) Field of Classification Search
  CPC .............. A61B 2090/365; A61B 34/20; A61B 2090/364; A61B 2034/2055; A61B 2034/2065
  See application file for complete search history.

(56) References Cited

U.S. PATENT DOCUMENTS

| | | | |
|---|---|---|---|
| 2013/0058555 A1* | 3/2013 | Miao | G06K 9/00214 382/132 |
| 2013/0094745 A1* | 4/2013 | Sundar | G06T 3/0068 382/132 |
| 2014/0050375 A1* | 2/2014 | Baker | A61B 34/20 382/128 |
| 2016/0117817 A1* | 4/2016 | Seel | A61B 90/37 382/131 |
| 2016/0163045 A1* | 6/2016 | Penney | G06T 11/003 382/131 |
| 2016/0335777 A1 | 11/2016 | Borsdorf et al. | |
| 2017/0178349 A1 | 6/2017 | Ketcha et al. | |

OTHER PUBLICATIONS

Zhang et al, "Hybrid Elastic Registration Using Constrained Free-Form Deformation," 2010 International Conference of Medical Image Analysis and Clinical Application (MIACA), pp. 75-78 (Year: 2010).*

Penney et al., "Deforming a Preoperative Volume To Represent the Intraoperative Scene", Computer Aided Surgery, 2002, vol. 7, No. 2, pp. 63-73, XP009032573.

Ketcha et al., "Multi-stage 3D-2D registration for correction of anatomical deformation in image-guided spine surgery", Physics in Medicine & Biology, IOP Publishing, 2017, vol. 62, No. 11, pp. 4604-4622, XP020317444.

Varnavas et al., "Fully automated 2D-3D registration and verification", Medical Image Analysis, 2015, vol. 26, No. 1, pp. 108-119, XP055599507.

Extended European Search Report for European Application No. 19166253.5, dated Jul. 12, 2019, 11 pages.

* cited by examiner

I. 2D-3D Registration at time i

Preoperative CT scan        Interventional table

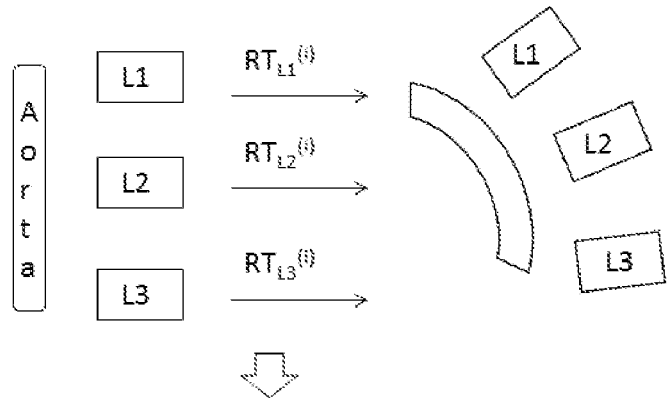

II. Compute observation of inter-vertebra movement

$$RT_{L1\text{-}L2}^{(i)} = \{RT_{L1}^{(i)}\}^{-1} RT_{L2}^{(i)}$$

$$RT_{L2\text{-}L3}^{(i)} = \{RT_{L2}^{(i)}\}^{-1} RT_{L3}^{(i)}$$

III. Compute observation of transformed vertebra related points

$$y_{L1,j}^{(i)} = RT_{L1\text{-}L2}^{(i)} x_{L1,j}^{(i)}$$

$$y_{L2,j}^{(i)} = RT_{L2\text{-}L3}^{(i)} x_{L2,j}^{(i)}$$

IV. Maximum Likelihood Estimation of transformed vertebra related points

$y_{L1,j}$ is computed using $y_{L1,j}^{(k)}$, $k = 0, \ldots, i$ $y_{L2,j}$ is computed using $y_{L2,j}^{(k)}$, $k = 0, \ldots, i$

V. Compute intervertebra movement using Procrustes Analysis

$RT_{L1\text{-}L2}$ is computed using point correspondences $(x_{L1,j}, y_{L1,j})$ $RT_{L2\text{-}L3}$ is computed using point correspondences $(x_{L2,j}, y_{L2,j})$

Fig. 1

I. Deform aortic surface:
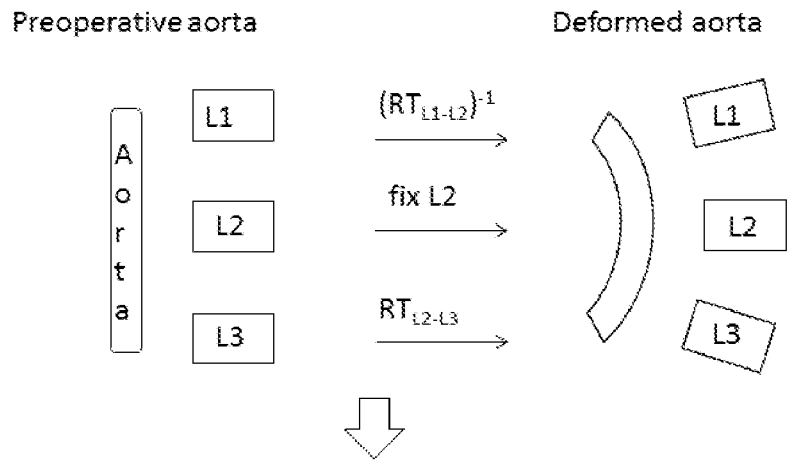
II. 2D-3D Registration:
The intraoperative pose for L1 is computed: $RT_{L1}$
III. Compute pose of fixed vertebra:
The intraoperative pose for L2 is computed: $RT_{L1} \cdot RT_{L1\text{-}L2}$
IV. Transform deformed aortic surface:
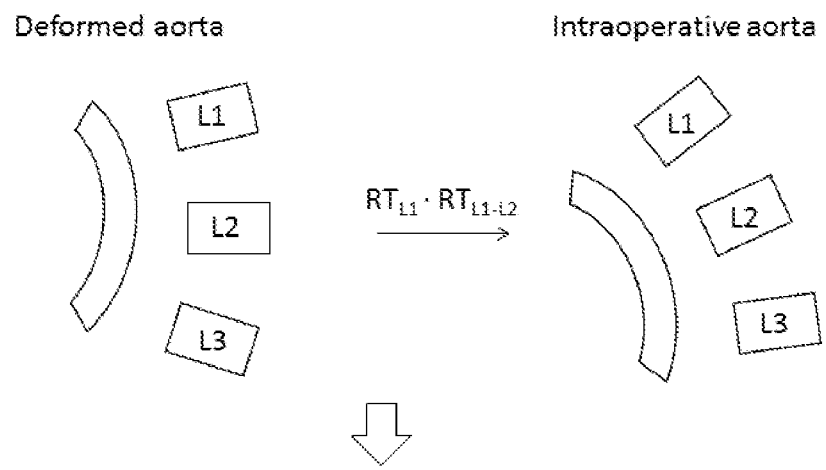
V. Project (overlay) intraoperative aorta on the fluoroscopy image
Fig. 2

I. GUI for user guided deformation:
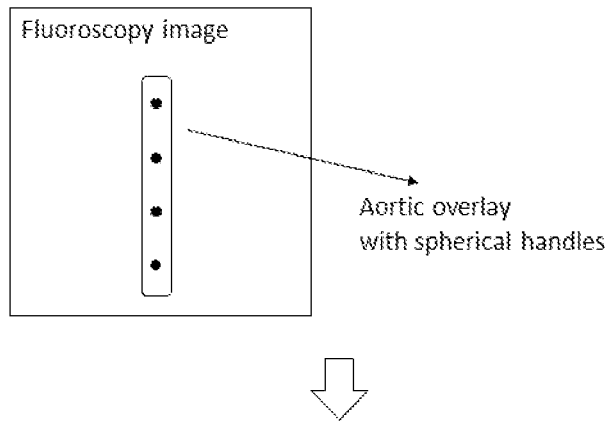
II. The user indicates aortic deformation:
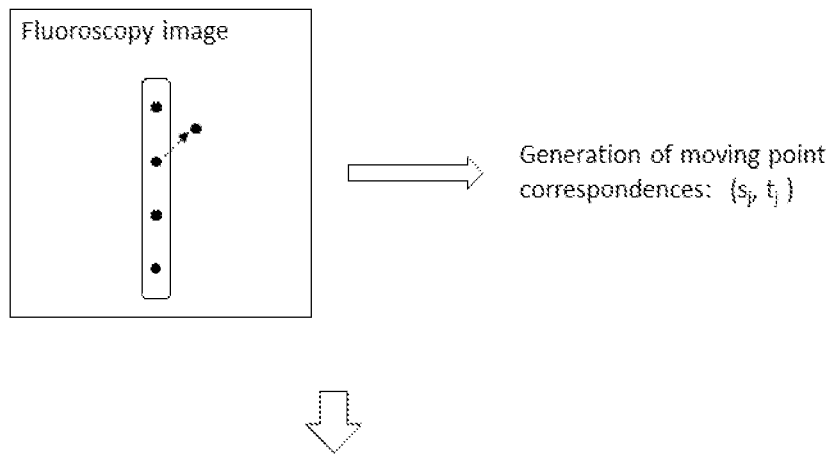
III. Thin Plate Spline based deformation of the aorta:
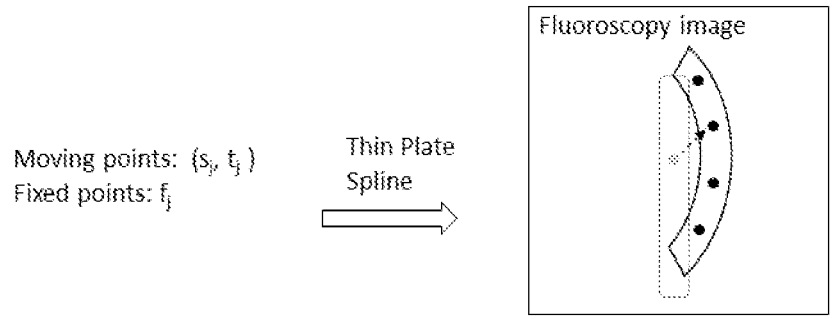
Fig. 3

US 10,977,812 B2

DEFORMATION CORRECTION

FIELD OF THE INVENTION

The present invention provides a method for monitoring the position of tissues in a body and correcting for deformations of these tissues during an operation that are caused by changes in the posture of a body and/or by interventional instruments.

BACKGROUND OF THE INVENTION

Minimally invasive surgical procedures guided by X-ray fluoroscopy such as cardiac ablation, neuroembolization, coronary artery angioplasty, and stent placement are widely used as they are advantageous compared to invasive surgical procedures, particularly for patients not suitable for open surgery.

Such procedures allow substantial reduction of infection risk and shorter recovery times because interventional fluoroscopy requires, comparatively, only a very small incision.

During fluoroscopy-guided endovascular interventions, low-dose X-ray (known as fluoroscopy screening) is used to provide guidance after inserting catheters, guide wires, or other interventional instruments into the patient's blood vessel by monitoring their movement in real-time on a set of display screens in the intervention room. However, only interventional devices and dense tissues such as bone are adequately visualized using fluoroscopy screening. Soft tissue anatomy such as the vasculature is not adequately visualized.

Prior to many types of operation a patient is typically subjected to a CT scan of the body area where the surgery will take place. This results in a three-dimensional image of the scanned body area. During surgery real time 2D fluoroscopy images are obtained of the same area, using for example a C-arm type fluoroscopy machine. These 2D fluoroscopy images may, however, be insufficient to allow a surgeon to determine the precise position within the body of surgical instruments or surgical implants, particularly during catheter based MIS procedures. For example, during stent-graft repair of aortic aneurysms, precise stent placement is essential.

In order to address the drawbacks of the 2D images, it is known to augment the 2D real time image with the 3D pre-obtained image, obtained, for example from a CT scan. The problem then arises of ensuring accurate registration of the 3D image with the 2D image i.e. ensuring that the 2D image is aligned with the correct parts of the 3D image. As is known already in the art, CT position and orientation is usually defined by six rigid body parameters, being three translations X, Y, and Z, and three rotations $\theta x$, $\theta y$, and $\theta z$. These can be divided into parameters which define movements parallel to the plane of the fluoroscopy image (in plane parameters $\theta x$, Y, and Z), and parameters which define movements a component of which is normal to the fluoroscopy plane (out-of-plane parameters $\theta y$, and $\theta z$, and X).

Furthermore, the pose and positioning of a subject will change between obtaining the 3D image data set and the 2D image. Necessarily, the position of tissues, and particularly soft tissues, will be moved or deformed because of the change in pose and/or positioning of the subject. Accordingly, a precise, rigid spatial transformation is inadequate to align the features visible in the 3-D image data set with the features of the 2-D image The registration problem is then one of how to manipulate these parameters such that the 3D image becomes aligned with the 2D image and then to adapt the aligned 3D image so that is accurately reflects the position of features that are partially visible or invisible in the 2D image. That is, the surgeon viewing the combined 2D and 3D images can have some confidence in the registration achieved and the features shown as coinciding.

Various registration techniques are known in the art. Specifically, in Penney et al "An Image-Guided Surgery System to Aid Endovascular Treatment of Complex Aortic Aneurysms: Description and Initial Clinical Experience", IPCAI 2011, LNCS 6689, pp. 13-24 the present inventors describe an intensity based registration technique which requires a starting position to be chosen by relying on visual inspection and identification of a vertebra in the fluoroscopy image. The present inventors also describe a method and apparatus for 2D-3D registration of a 3D image dataset (a CT scan) with an X-ray fluoroscopy image in International patent application no. WO 2013/132235.

OBJECT OF THE INVENTION

There is a need for an improved method for adapting pre-operative medical images so that they can be accurately registered and combined with intra-operative medical images in order to improve the accuracy of placement of surgical devices. This is especially the case for minimally invasive surgery procedures. There is also a need to address the problem that a rigid spatial translation may not allow for pose changes posture changes or other deformations during surgery.

SUMMARY OF THE INVENTION

Embodiments of the invention are intended to provide alternative solutions to and/or to address one or more of the problems described above.

Accordingly the invention provides a method for determining the change in relative position of a feature of a subject recorded in a 3-D image dataset resulting from movement of the subject, comprising the steps of:
 (a) providing a first, 3D image dataset of the subject;
 (b) obtaining one or more second, 2D image datasets of the subject, wherein the subject has been moved in the time between creating the first and second image datasets;
 (c) defining at least a first feature and a second feature that are detected in both first and second image datasets;
 (d) performing a first 2D-3D registration between the first feature shown in the second image and the first feature shown in the first image and thus determining the movement of the first feature between the two images;
 (e) performing a second 2D-3D registration between the second feature shown in the second image and the second feature shown in the first image and thus determining the movement of the second feature between the two images;
 determining a first transformation describing the relative movement of the first feature with respect to the second feature caused by moving the subject;
 (g) defining the position of at least a third feature in the first image dataset and determining the position of this third feature relative to the first feature;
 (h) defining the position of at least a fourth feature in the first image dataset and determining the position of this fourth feature relative to the second feature;
 (i) fixing the position of the second feature and applying the first transformation to the third feature of the first image to yield a first set of spatial point correspondences between the third and fourth features and the transformed third and fourth features;

(j) determining an interpolation function on the basis of the first set of spatial point correspondences;

(k) defining at least a fifth feature that is detected in the first image dataset and applying the interpolation function to its position.

The invention also provides an image guided surgical system, comprising:

a 2D imaging system arranged in use to obtain one or more second 2D image datasets to be registered with a first, 3D image data set, wherein the object is moved between obtaining the 3D image data set and the 2D image; and a processor, arranged in use to:

(a) define at least a first feature and a second feature that are detected in both first and second image datasets;

(b) perform a first 2D-3D registration between the first feature shown in the second image and the first feature shown in the first image and thus determine the movement of the first feature between the two images;

(c) perform a second 2D-3D registration between the second feature shown in the second image and the second feature shown in the first image and thus determine the movement of the second feature between the two images;

(d) determine a first transformation describing the relative movement of the first feature with respect to the second feature caused by moving the subject;

(e) define the position of at least a third feature in the first image dataset and determine the position of this third feature relative to the first feature;

(f) define the position of at least a fourth feature in the first image dataset and determine the position of this fourth feature relative to the second feature;

(g) fix the position of the second feature and apply the first transformation to the third feature of the first image to yield a first set of spatial point correspondences between the third and fourth features and the transformed third and fourth features;

(h) determine an interpolation function on the basis of the first set of spatial point correspondences;

(i) define at least a fifth feature that is detected in the first image dataset in the first image dataset and apply the interpolation function to its position.

The method may be applied to multiple pairs of first and second features. In this way a chain of transformations (described in the form of matrices) describing the movement of pairs of first and second features may be determined. Therefore, advantageously, the method may be used to describe the relative movement of all or part of the spine of a subject.

The movement the subject undergoes between obtaining the 3D image data set and the 2D image dataset is can preferably be described as a non-rigid transformation.

The first and second features may each be visible individually or visible together in any of the one or more second, 2D image datasets of the subject.

The first and second features of the aspects of the invention described herein may be vertebrae. Preferably the pairs of vertebrae are adjacent to one another.

Fluoroscopy is particularly suitable for locating and viewing parts of the anatomy that do not easily deform or deform substantially less than other features, e.g. bones. The quality of not deforming means that the location of these features of the anatomy can be consistently and accurately determined when surrounding softer tissues have deformed over time or during an operation.

The position of the fifth feature of the subject may be predicted from or influenced by the positions of the first and second features of the subject. That is, the first and second features may act as surrogates that are visible on a fluoroscopy image which show the position of features of anatomy that are otherwise invisible or partially visible on a fluoroscopy image.

The fifth feature may be a soft tissue. For example the fifth feature may be a blood vessel and/or a junction between blood vessels and/or the inner or outer surface of a blood vessel. Most preferably the fifth feature is the aorta.

Thus the fifth feature may be defined as a volume or geometrically described shape or object in order to define a particular tissue, organ or structure of the subject. Preferably the fifth feature is within the subject.

The interpolated position of the fifth feature may be marked on the second image dataset. Marking the fifth feature on the second image dataset may be achieved by various means. Preferably, volumes or surfaces derived from the first image dataset are overlaid on to the second image dataset. Alternatively, the second image dataset may be marked with points or targets. As a further alternative the second image dataset may be marked with wireframe diagrams in order to indicate the extent of volumes or geometric forms in the first image dataset.

Preferably, one or more of the images is a digital image. While other forms of image may be used with the invention, digitised images, and especially native digital images are particularly preferred.

The 3D data set can be obtained as part of the image generation in carrying out the method. It is also optional to use a 3D data set obtained otherwise, e.g. in advance.

The 3D image data set may be obtained from a computerised tomography (CT), magnetic resonance (MR) or cone beam computerised tomography scan (CBCT).

Preferably, the 3D image data set is obtained via a computerised tomography (CT) scan.

Computerised tomography is particularly suitable for use with the invention because it is suitable for accurately locating and viewing parts of the anatomy that do not easily deform, e.g. bones, as well as the surrounding softer tissue. Accuracy in locating features of anatomy that appear in 2D fluoroscopy images and 3D CT scans allows better (e.g. more accurate and more quickly achieved) 2D-3D registration of 2D fluoroscopy scans with 3D CT scans.

Other 2D-3D registration techniques are known and are suitable for use in the context of this invention. In particular the method disclosed in WO 2013/132235. Other methods include tracking of the C-arm and table after an initial registration process. The initial registration process can be carried out either automatically, semi-automatically or manually to either a 2D image or images, or a 3D image (e.g. CBCT) acquired in theatre.

The 2D-3D registration technique described in WO 2013/132235 is particularly suitable for use in the context of this invention. This is because this technique allows automatic checking between images; there is no need for a technician to manually align the different image.

In addition, an advantage of the methods described herein is that no non-standard equipment is required in the operating theatre. The computer or computers, used for the 2D-3D image registration can also be used for the deformation correction methods of the invention.

The first and second registrations may be repeated to give rise to multiple observations of the first transformation. The first transformation may then be determined from this population of observations. Thus, advantageously, multiple registrations can be found and their results pooled to form a population in order that subsequent analysis can provide a more accurate first transformation.

The pooled set of transformations may be combined by applying Maximum Likelihood Estimation to a set of points transformed by the set of transformations.

It is envisaged that other methods for obtaining a representative value from a population of data points can be used in the context of the present invention. The specific alternative method to be used depends on the data being analysed and more particularly on the frequency distribution of the data points and/or model for estimating or ascertaining the degree of noise in the data.

The first transformation may be found by employing Procrustes analysis on the first set of spatial point correspondences. Procrustes analysis is an advantageous method as it is suitable for analysing rigid motion. Alternatively, an affine transformation matrix found using least squares may also be used.

The first transformation may be defined in terms of x, y and z coordinates and rotation about the x, y and z axes (being, being three translations X, Y, and Z, and three rotations $\theta x$, $\theta y$, and $\theta z$).

The first transformation may be applied as a rigid transformation. This has the advantage of being a relatively simple calculation thus providing a result efficiently. Rigid transformations are particularly suitable in the context of the present invention wherein the first and second features are rigid objects, preferably vertebrae.

A variety of interpolation functions may be used in the context of the present invention. For example, a radial basis function such as a Thin Plate Spline interpolating function. Preferably, the interpolation function is a Thin Plate Spline interpolating function.

Thus according to the aspects of the invention described herein, the invention advantageously provides a method for adapting 3D image datasets so that they can be registered and combined with 2D images of the same subject, wherein deformation or movement of parts of the subject has occurred between obtaining the 3D image and the 2D image.

The method of determining the interpolation function may comprise the further steps of
  defining a point in the first image dataset;
  mapping the point in the first image dataset to the corresponding point in the second image dataset by performing a 2D-3D registration between the datasets;
  moving the point in the second image data set to a new location and moving the corresponding point in the first image dataset in accord;
  defining a second set of spatial point correspondences between the original and new point locations in the first and second image datasets;
  determining the interpolation function on the combined basis of the first and second sets of spatial point correspondences.

It is envisaged in an alternative embodiment of the invention that mapping the point in the second image dataset to the corresponding point in the first image dataset may be achieved by applying the interpolation function.

In the methods described herein further points may be defined at further locations in the first image dataset, and preferably the points are arranged in a straight or curved line at equal intervals. In preferred embodiments 1, 2, 3, 4, 5, 6, 7, 8, 9, 10, 11, 12, 13, 14, 15, 16, 17, 18, 19, 20, 25, 30, 35, 40, 45 or 50 points are used. Preferably 20 points are used. Most preferably the points are about 4 cm apart.

Thus according to the aspects of the invention described herein, the invention further advantageously provides methods for adapting the first image dataset according to movement that is detected in the second image dataset as having occurred since the creation of the first image dataset. This is achieved by defining and moving points in the second image dataset such that the first image dataset is adapted in concert and the interpolation function re-determined accordingly.

The points of the set of spatial point correspondences may be defined as vectors.

The first, 3D image dataset may be a computed tomography (CT) scan. The second, 2D image dataset may be a fluoroscopy image, preferably an X-ray image.

The third and fourth features of the aspects of the invention described herein may be grids of points forming first and second planes, respectively, preferably the third and fourth features lie in the first and second planes, respectively. Preferably, the grids of points are regularly spaced. Most preferably, the grids of points are rectangular.

The grids of points forming the first and second planes may be orthogonal to the direction of the spine at the individual vertebra. Preferably the centroids of the first and second vertebrae lie in the first and second planes, respectively.

The fifth feature of the aspects of the invention described herein may lie in one or both of the first and second planes. Preferably the fifth feature projects through one or both of the first and second planes.

Image guided surgical systems comprising a processor may be arranged to the methods disclosed herein.

DESCRIPTION OF THE DRAWINGS

The invention is now illustrated in the following specific embodiments with reference to the accompanying drawings.

FIG. 1 is a schematic depicting Step 1A of the method of deformation correction described herein, comprising the stages of:
  I. The rigid transformation between the CT scan and the subject on the operating table under an arbitrary pose of the C-arm is computed in time i.
  II. An observation of the intervertebra movement is computed.
  III. The observation of the intervertebra movement gives rise to an observation of the vertebra related target auxiliary points.
  IV. Maximum likelihood estimation is used to estimate the target auxiliary points using all observations until time i.
  V. The intervertebra movement is computed through Procrustes Analysis, using the correspondences between source and target auxiliary points.

FIG. 2 is a schematic depicting Step 1B of the method of deformation correction described herein, comprising the stages of:
  I. The intervertebra movement of vertebrae L1, L2, L3 is described by RTL1-L2 and RTL2-L3. Assuming that vertebra L2 remains fixed the corresponding transformations for L1 and L3 are computed. The aorta is deformed using a Thin Plate Spline interpolator which is instantiated based on the rigid transformation of the vertebrae.

II. The C-arm pose dependent transformation of L1 is recovered through vertebra based 2D-3D registration using the preoperative CT scan and the intraoperative fluoroscopy image.

III. The corresponding pose of L2 is then computed using RTL1-L2 which describes the movement between the two vertebrae.

IV. This pose is then used to transform the deformed aorta.

V. The transformed aorta is then overlaid on the fluoroscopy image.

FIG. 3 is a schematic depicting Step 2 of the method of deformation correction described herein, comprising the stages of:

I. The GUI with the aortic overlay on the intraoperative fluoroscopy image.

II. Spherical handles are overlaid along the centre line of the aorta.

II. The user indicates the aortic deformation by moving the handles. Associated moving point correspondences are generated.

III. The moving point correspondences together with the predefined fixed points instantiate a Thin Plate Spline which is used to deform the aorta.

EXAMPLE

Described herein is a system used to non-rigidly deform the patient's preoperative CT aortic surface according to the way the patient's aorta has been deformed during the course of a minimally invasive procedure. The system estimates the intra-operative aortic deformation in two steps:

1) A fully automated step, during which the aortic deformation caused by the change in the patient's posture between the CT scan and the operating table is estimated. This estimation is carried out by first estimating the change in the patient's posture, i.e. the rigid movement of one vertebra relative to another (inter-vertebra movement). This movement is then used to non-rigidly deform the aorta, such that the closer a part of the aorta is to a certain vertebra, the more its deformation is influenced by the movement of this vertebra.

2) A semi-automatic step, during which the aortic deformation caused by the interventional instruments is estimated. During this step a Graphical User Interface showing the aorta overlaid on an intraoperative X-ray image is employed to allow the user to indicate how the aorta has been deformed. The input of the user deforms the aorta in real time, so the user can indicate the deformation which produces an aortic overlay that best agrees with interventional instruments, contrast or any other entities on the X-ray image which are related to the intraoperative shape of the aorta.

Step 1 is repeated in the background every time new observations of the rigid transformation of the patient's vertebrae between the preoperative CT scan and the operating table are available. Step 2 is employed upon user request, usually when an x-ray image with useful information about the intraoperative shape of the aorta is available. Accordingly, use of Step 2 is optional during the procedures described in this example.

Step 1A: Automated Estimation of Change in Patient's Posture

The change in patient's posture between the CT scan acquisition and the operating table is quantified by estimating the rigid movement of each vertebra relative to its neighbouring vertebrae. For two neighbouring vertebrae A and B this movement is described by matrix $RT_{AB} = RT_A^{-1} RT_B$, where $RT_A$ and $RT_B$ are the rigid transformation (4×4) matrices describing the transformation of vertebrae A and B, between the CT scan and the operating table under an arbitrary pose of the C-arm of the fluoroscopy set. It is noted that although $RT_A$ and $RT_B$ depend on the pose of the C-arm of the fluoroscopy set, matrix $RT_{AB}$ is independent of such pose.

During the course of a medical procedure, a 2D-3D registration process between the intraoperative fluoroscopy image and the preoperative CT scan is being used to compute multiple pairs of $RT_A$ and $RT_B$, with their instances corresponding to time i being denoted as $RT_A^{(i)}$ and $RT_B^{(i)}$. Each pair $RT_A^{(i)}$, $RT_B^{(i)}$ gives rise to a noisy observation $RT_{AB}^{(i)}$ of $RT_{AB}$. The error in $RT_{AB}^{(i)}$ is due to the registration error during the computation of $RT_A^{(i)}$ and $RT_B^{(i)}$.

Matrix $RT_{AB}$ is estimated from multiple observations $RT_{AB}^{(i)}$ in the following way:

1) A set of 3D points $x_j$ on the vertices of a cube enclosing vertebra A are selected in preoperative CT coordinates.

2) For each observation $RT_{AB}^{(i)}$ a corresponding observation $y_j^{(i)} = RT_{AB}^{(i)} x_j$ is produced.

3) We assume that the registration error in $RT_A^{(i)}$ and $RT_B^{(i)}$ is only in the translational component and that it is additive, following a Gaussian distribution with zero mean and covariance matrix C. We also assume that the registration error of vertebra A is uncorrelated with the registration error of vertebra B. Under these assumptions the error in each observation $y_j^{(i)}$ is additive, Gaussian with zero mean and a covariance matrix equal to $G_i = R_{Ai}^{-1} 2C(R_{Ai}^{-1})^T$, where $R_{Ai}$ is the rotation matrix corresponding to vertebra A under the pose of the C-arm in time i.

4) The value of each point $y_j$ is estimated employing Maximum Likelihood Estimation on its observations and assuming that the registration error across different times i is uncorrelated.

5) Matrix $RT_{AB}$ is computed using Procrustes analysis on the point correspondences $x_j$, $y_j$.

The above procedure is repeated every time a 2D-3D registration with respect to two adjacent vertebrae is performed. In this way a chain of matrices describing the movement of adjacent vertebrae is computed and continuously kept updated during the medical procedure. It is noted that this movement is between the CT acquisition and the operating table.

Step 1B: Automated Correction of Aortic Deformation Caused by Change in Patient's Posture The estimated intervertebra movement calculated in step 1A is used to deform the preoperative surface of the aorta in the following way:

1) The direction of the preoperative spine is computed by summing up the normalised vectors which connect the centroids of each pair of adjacent vertebrae.

2) For each vertebra, a plane is considered, which is perpendicular to the direction of the spine and which goes through the centroid of the vertebra.

3) A regular and rectangular grid of points is applied on each plane. The boundaries of the grid are determined such that the projection of every point of the aortic surface on the plane is within the boundaries of the grid.

4) Assuming a certain vertebra fixed, a rigid transformation is computed for each of the rest of the vertebrae using the estimated intervertebra movement.

5) The points on the grid of each plane are transformed using the rigid transformation of the corresponding vertebra. The original together with the transformed points form a set of point correspondences which is used to instantiate a Thin Plate Spline interpolating function. This function is used to deform the preoperative aortic surface.

The deformed aortic surface is overlaid on an intraoperative fluoroscopy image in the following way.
1) A vertebra based 2D-3D registration process is first used to compute the rigid transformation of a specific vertebra between the preoperative CT scan and the operating table under the pose of the C-arm of the fluoroscopy set.
2) This transformation is combined with the estimated intervertebra movement to compute the corresponding transformation for the vertebra assumed fixed in the process of deforming the aortic surface (see point 4 above).
3) The computed transformation is used to rigidly transform the deformed surface. The surface is then projected on the fluoroscopy image.

The described process of deforming the aorta is fully automated and can be applied continuously during the operation in order to make use of the updated (refined) estimation of the intervertebra movement.

Step 2: Automated Correction of Aortic Deformation Caused by Interventional Instruments The correction of the aortic deformation caused by interventional instruments is done in a semi-automatic manner through a Graphical User Interface (GUI). The main elements of the GUI are:
1) An intraoperative fluoroscopy image which preferably contains some indications about the way the aorta has been deformed intraoperatively. Examples of such indications are: injected contrast, visible calcium in the aorta, catheters, stents or other interventional instruments.
2) A projection of the aortic surface overlaid on the fluoroscopy image. This is the preoperative aortic surface which has potentially been deformed through calls of Step 1B and/or previous calls of Step 2. This deformed surface is rigidly transformed to agree with the pose of the C-arm of the fluoroscopy set, using a rigid transformation, which is computed through vertebra based 2D-3D registration between the preoperative CT scan and intraoperative fluoroscopy image.
3) A set of handles (e.g. spherical blobs) overlaid on the fluoroscopy image along the centre line of the aorta. An example of the spacing between the handles can be the distance between adjacent vertebrae, i.e. ~4 cm.
4) The opacity of the overlaid aortic surface can be adjusted by the user, such that the handles and the area of the fluoroscopy image under the surface are clearly visible.

A user (e.g. surgeon, radiographer, nurse) can use the handles to indicate how the aorta has been deformed. This is done in the following way:
1) The user selects a handle close to the area where the deformation has occurred.
2) The user can translate the handle or carry out an in-plane rotation with it.
3) The movement of the handle indicates a corresponding movement of associated points in CT scan coordinates, producing a set of moving point correspondences. A second set of points, selected in areas of bone (e.g. centroids of vertebrae), are assumed fixed, consisting a set of fixed point correspondences. The two sets of point correspondences are used to instantiate a Thin Plate Spline interpolator. This interpolator is used to deform the aortic surface accordingly.
4) Each time a user moves a handle, the set of point correspondences is modified and the indicated aortic deformation and the aortic overlay are updated accordingly. This enables the user to continue moving a handle until the aorta is deformed in the desired way (i.e. its shape is aligned with relevant elements on the fluoroscopy image). If necessary multiple handles can be moved by the user.
5) When the user is satisfied, they terminate the GUI and the deformed aorta is saved for subsequent use. The overlays produced from that point on make use of this deformed aorta.

Combined Use of Step 1 and Step 2

Step 1 and Step 2 can be employed multiple times during the course of an operation to gradually and cooperatively correct the shape of the aorta. The two steps can be employed together in the following way:
1) The deformation carried out by the user in Step 2 is defined by the movement of the points in the CT scan, associated with the handles in the GUI, and by the points in the CT scan which are assumed fixed. Let us denote with sj and tj the source and target CT coordinates of the moving points and with fj the CT coordinates of the fixed points.
2) Every time Step 1 is used and the aorta is deformed as described in Step 1B, the coordinates sj and fj are also transformed using the same method, producing new coordinates sj' and fj' respectively. If Step 2 has previously been used, the aorta is further deformed (as described in Step 2) by a Thin Plate Spline Interpolator by using the moving point correspondences (sj', tj) and the fixed points fj'.
3) This is also the case for subsequent calls of Step 2. The related GUI shows the most recent version of the deformed aorta but the Thin Plate Spline Interpolator of Step 2 acts on the preoperative aorta as it has been deformed by the most recent call of Step 1. The Thin Plate Spline interpolator is instantiated using the moving point correspondences (sj', tj) and the fixed points fj'. Let us repeat that the target points tj are indicated by the move of the handles and the source and fixed points sj' and fj' have been corrected for intervertebra movement by the most recent call of Step 1.

The invention thus provides methods and apparatus for improving the accuracy of locating tissues that move or are deformed between obtaining a 3D image dataset of a subject and subsequent 2D images of the subject.

We claim:
1. A method for determining the change in relative position of a feature of a subject recorded in a 3D image dataset resulting from movement of the subject, comprising:
(a) providing a first, 3D image dataset of the subject;
(b) obtaining one or more second, 2D image datasets of the subject, wherein the subject has been moved in the time between creating the first and second image datasets;
(c) defining at least a first feature and a second feature that are detected in both first and second image datasets;
(d) performing a first 2D-3D registration between the first feature shown in the second image and the first feature shown in the first image and thus determining the movement of the first feature between the two images;
(e) performing a second 2D-3D registration between the second feature shown in the second image and the second feature shown in the first image and thus determining the movement of the second feature between the two images;
(f) determining a first transformation describing the relative movement of the first feature with respect to the second feature caused by moving the subject;
(g) defining the position of at least a third feature in the first image dataset and determining the position of this third feature relative to the first feature;
(h) defining the position of at least a fourth feature in the first image dataset and determining the position of this fourth feature relative to the second feature;
(i) fixing the position of the second feature and applying the first transformation to the third feature of the first image to yield a first set of spatial point correspondences between the third and fourth features and the transformed third and fourth features;
(j) determining an interpolation function on the basis of the first set of spatial point correspondences, wherein the method of determining the interpolation function further comprises:
defining a point in the first image dataset;
mapping the point in the first image dataset to the corresponding point in the second image dataset by performing a 2D-3D registration between the datasets;
moving the point in the second image data set to a new location and moving the corresponding point in the first image dataset in accord;
defining a second set of spatial point correspondences between the original and new point locations in the first and second image datasets;
determining the interpolation function on the combined basis of the first and second sets of spatial point correspondences;
(k) defining at least a fifth feature that is detected in the first image dataset in the first image dataset and applying the interpolation function to its position.

2. The method of claim 1, wherein the interpolated position of the fifth feature is marked on the second image dataset.

3. The method of claim 1, wherein the first and second registrations are repeated and the first transformation is determined from this population of registration coordinates.

4. The method of claim 1, wherein the first and second registrations are determined by applying Maximum Likelihood Estimation to the population of registration coordinates.

5. The method of claim 1, wherein the first transformation is found by employing Procrustes analysis on the first set of spatial point correspondences.

6. The method of claim 1, wherein the first transformation is applied as a rigid transformation.

7. The method of claim 1, wherein the interpolation function is a Thin Plate Spline interpolating function.

8. The method of claim 1, wherein further points are defined at further locations in the first image dataset.

9. The method of claim 1, wherein the points of the set of spatial point correspondences are defined as vectors.

10. The method of claim 1, wherein the first, 3D image dataset is a computed tomography (CT) scan.

11. The method of claim 1, wherein the second, 2D image dataset is a fluoroscopy image.

12. The method of claim 1, wherein the first and second features are vertebrae.

13. The method of claim 1, wherein the third and fourth features are grids of points forming first and second planes, respectively.

14. The method of claim 1, wherein the grids of points forming the first and second planes are orthogonal to the direction of the spine at the individual vertebra.

15. The method of claim 1, wherein the fifth feature lies in one or both of the first and second planes.

16. The method of claim 1, wherein the fifth feature is a soft tissue.

17. The method of claim 1, wherein the fifth feature is a blood vessel.

18. An image guided surgical system, comprising:
a 2D imaging system arranged to obtain one or more second 2D image datasets to be registered with a first, 3D image data set, wherein the subject is moved between obtaining the 3D image data set and the 2D image; and
a processor, arranged to:
(a) define at least a first feature and a second feature that are detected in both first and second image datasets;
(b) perform a first 2D-3D registration between the first feature shown in the second image and the first feature shown in the first image and thus determine the movement of the first feature between the two images;
(c) perform a second 2D-3D registration between the second feature shown in the second image and the second feature shown in the first image and thus determine the movement of the second feature between the two images;
(d) determine a first transformation describing the relative movement of the first feature with respect to the second feature caused by moving the subject;
(e) define the position of at least a third feature in the first image dataset and determine the position of this third feature relative to the first feature;
(f) define the position of at least a fourth feature in the first image dataset and determine the position of this fourth feature relative to the second feature;
(g) fix the position of the second feature and apply the first transformation to the third feature of the first image to yield a first set of spatial point correspondences between the third and fourth features and the transformed third and fourth features;
(h) determine an interpolation function on the basis of the first set of spatial point correspondences, wherein determining the interpolation function further comprises:
defining a point in the first image dataset;
mapping the point in the first image dataset to the corresponding point in the second image dataset by performing a 2D-3D registration between the datasets;
moving the point in the second image data set to a new location and moving the corresponding point in the first image dataset in accord;
defining a second set of spatial point correspondences between the original and new point locations in the first and second image datasets;
determining the interpolation function on the combined basis of the first and second sets of spatial point correspondences;
(i) define at least a fifth feature that is detected in the first image dataset in the first image dataset and apply the interpolation function to its position.

19. The image guided surgical system of claim 18, wherein the processor is further arranged to determine the change in relative position of a feature of a subject recorded in a 3D image dataset resulting from movement of the subject.

* * * * *